(12) United States Patent
Tartaggia et al.

(10) Patent No.: US 9,238,613 B2
(45) Date of Patent: Jan. 19, 2016

(54) INTERMEDIATE COMPOUNDS AND DERIVATIVES THEREOF INVOLVED IN THE PREPARATION OF 2,4,5-TRIFLUOROPHENYLACETIC ACID COMPOUNDS AND DERIVATIVES THEREOF

(71) Applicant: F.I.S.—Fabrica Italiana Sintetici S.p.A., Alte di Montecchio Maggiore (IT)

(72) Inventors: Stefano Tartaggia, Vicenza (IT); Andrea Caporale, Vicenza (IT); Ottorino De Lucchi, Vicenza (IT)

(73) Assignee: F.I.S.—Fabrica Italiana Sintetici S.p.A., Vicenza (IT)

( * ) Notice: Subject to any disclaimer, the term of this patent is extended or adjusted under 35 U.S.C. 154(b) by 0 days.

(21) Appl. No.: 14/457,417

(22) Filed: Aug. 12, 2014

(65) Prior Publication Data
US 2014/0350287 A1   Nov. 27, 2014

Related U.S. Application Data

(62) Division of application No. 13/753,701, filed on Jan. 30, 2013, now Pat. No. 8,835,679.

(30) Foreign Application Priority Data

Jan. 31, 2012  (IT) .............................. MI2012A0114

(51) Int. Cl.
| | |
|---|---|
| C07C 43/12 | (2006.01) |
| C07C 69/76 | (2006.01) |
| C07C 69/63 | (2006.01) |
| C07C 41/08 | (2006.01) |
| C07C 43/176 | (2006.01) |
| C07C 51/09 | (2006.01) |
| C07C 17/04 | (2006.01) |
| C07C 25/13 | (2006.01) |
| C07C 25/24 | (2006.01) |
| C07C 17/18 | (2006.01) |
| C07C 17/25 | (2006.01) |
| C07C 67/00 | (2006.01) |
| C07C 69/65 | (2006.01) |
| C07C 45/46 | (2006.01) |
| C07C 49/80 | (2006.01) |
| C07C 51/00 | (2006.01) |
| C07C 25/28 | (2006.01) |
| C07C 67/39 | (2006.01) |
| C07C 69/635 | (2006.01) |

(52) U.S. Cl.
CPC ................. *C07C 69/63* (2013.01); *C07C 17/04* (2013.01); *C07C 17/18* (2013.01); *C07C 17/25* (2013.01); *C07C 25/13* (2013.01); *C07C 25/24* (2013.01); *C07C 25/28* (2013.01); *C07C 41/08* (2013.01); *C07C 43/12* (2013.01); *C07C 43/176* (2013.01); *C07C 45/46* (2013.01); *C07C 49/80* (2013.01); *C07C 51/00* (2013.01); *C07C 51/09* (2013.01); *C07C 67/00* (2013.01); *C07C 67/39* (2013.01); *C07C 69/635* (2013.01); *C07C 69/65* (2013.01)

(58) Field of Classification Search
CPC ....................................................... C07C 17/18
USPC ............................................................ 562/496
See application file for complete search history.

(56) References Cited

U.S. PATENT DOCUMENTS 3,957,891 A *   5/1976  Gelfand ......................... 570/185
2010/0167924 A1 *  7/2010  Dietz et al. .................... 504/100

* cited by examiner

*Primary Examiner* — Yong Chu
*Assistant Examiner* — Ana Z Muresan
(74) *Attorney, Agent, or Firm* — Thomas|Horstemeyer, LLP

(57) ABSTRACT

Described herein are intermediate compounds and derivatives thereof that can be synthesized during the preparation of 2,4,5-trifluorophenylacetic acid and derivatives thereof.

3 Claims, 2 Drawing Sheets

Figure 1:
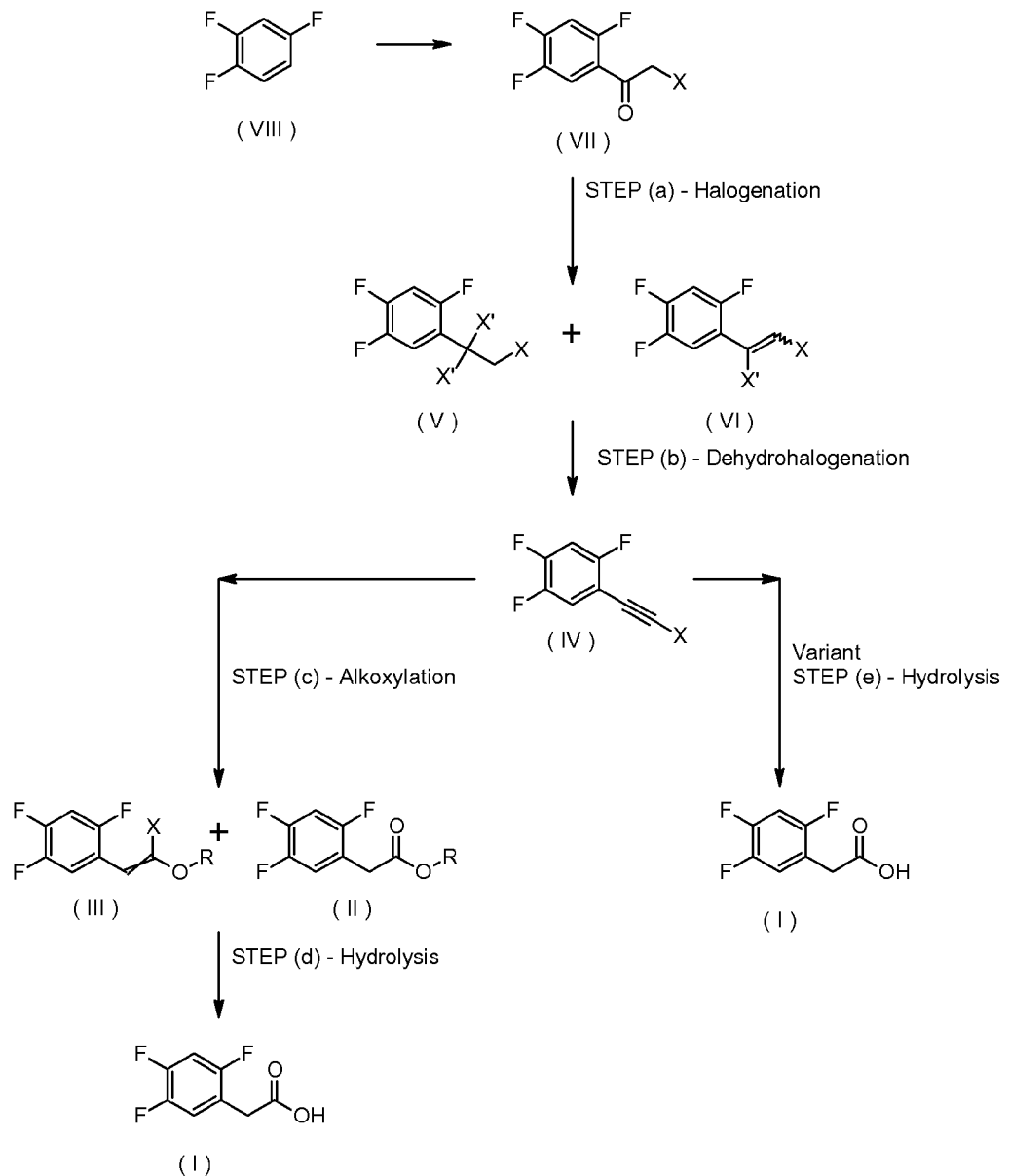

INTERMEDIATE COMPOUNDS AND DERIVATIVES THEREOF INVOLVED IN THE PREPARATION OF 2,4,5-TRIFLUOROPHENYLACETIC ACID COMPOUNDS AND DERIVATIVES THEREOF

CROSS-REFERENCE TO RELATED APPLICATIONS

This application claims priority to and is a divisional of U.S. Non-Provisional application entitled, "NEW PROCESS FOR THE PREPARATION OF 2,4,5-TRIFLUOROPHENY-LACETIC ACID", having Ser. No. 13/753,701, filed on Jan. 30, 2013, which claims benefit of Italian patent application MI2012A000114, filed Jan. 31, 2012, which both are entirely incorporated herein by reference.

TECHNICAL FIELD OF THE INVENTION

The present invention relates to a process for the preparation of 2,4,5-trifluorophenylacetic acid and salts thereof.

STATE OF THE ART

Fluorophenylacetic acids are useful intermediates for the preparation of various pharmacologically active compounds. In particular trifluorophenylacetic acids are used in the preparation of inhibitors of the dipeptidyl peptidase-4 enzyme. These medicines are useful in treating diabetes, in particular type 2 diabetes (see for example WO 97/40832; WO 98/19998; U.S. Pat. No. 5,939,560; *Bioorg. Med. Chem. Lett.*, 6, 1163-1166 (1996); *Bioorg. Med. Chem. Lett.*, 6, 2745-2748 (1996))
One of these active ingredients is Sitagliptin, available commercially under the brand name Januvia, which uses 2,4,5-trifluorophenylacetic acid as a key intermediate for its synthesis.

US 20040068141 claims a process for the preparation of fluorophenylacetic acids starting from aromatic halides according to the method described in diagram 1 (X represents chlorine, bromine or iodine):

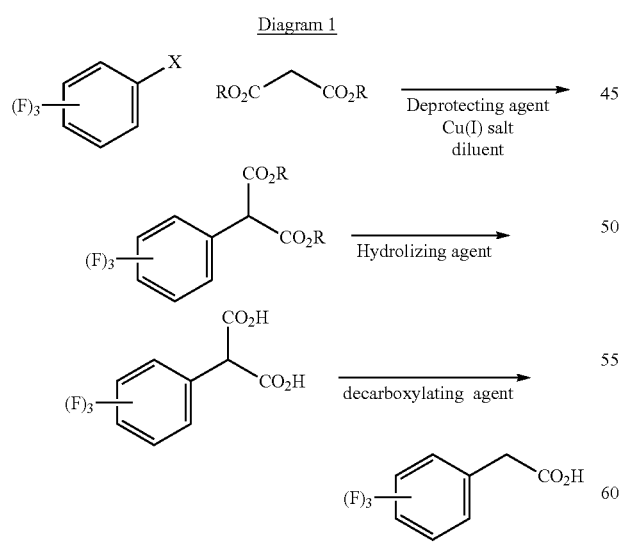

Diagram 1

The first step however requires the use of large quantities of copper salts, with obvious problems of extraction and disposal of the heavy metal, and the aromatic halide used often has elevated costs.

U.S. Pat. No. 5,306,833 claims a process for the preparation of phenylacetic acids substituted on the aromatic ring with electron donor groups by reduction of corresponding mandelic acids. In particular p-hydroxyphenylacetic acid is obtained starting from sodium p-hydroxymandelate and p-methoxyphenylacetic acid is obtained starting from sodium p-methoxymandelate. However such method is applicable only to electron rich substrates and does not work with substrates with electron attractor substitutes such as fluorine.

In the application WO2008078350 a process is described composed of various steps of synthesis for the preparation of fluorophenylacetic acids and their derivatives, in particular of 2,4,5-trifluorophenylacetic acid, starting from corresponding mandelic acids.

SUMMARY OF THE INVENTION

The problem addressed by the present invention is that of making available an alternative process for the preparation of 2,4,5-trifluorophenylacetic acid and salts thereof, by means of new synthetic intermediates, which makes it possible to at least partially overcome the drawbacks presented above in relation to the prior art.

Such problem is resolved by a process of synthesis of 2,4,5-trifluorophenylacetic acid as delineated in the appended claims, the definitions of which form an integral part of this description.

Further characteristics and advantages of the process according to the invention will be evident from the description below of its preferred embodiments made by way of non-limiting examples.

BRIEF DESCRIPTION OF THE FIGURES (OR DRAWINGS)

Figure 2:
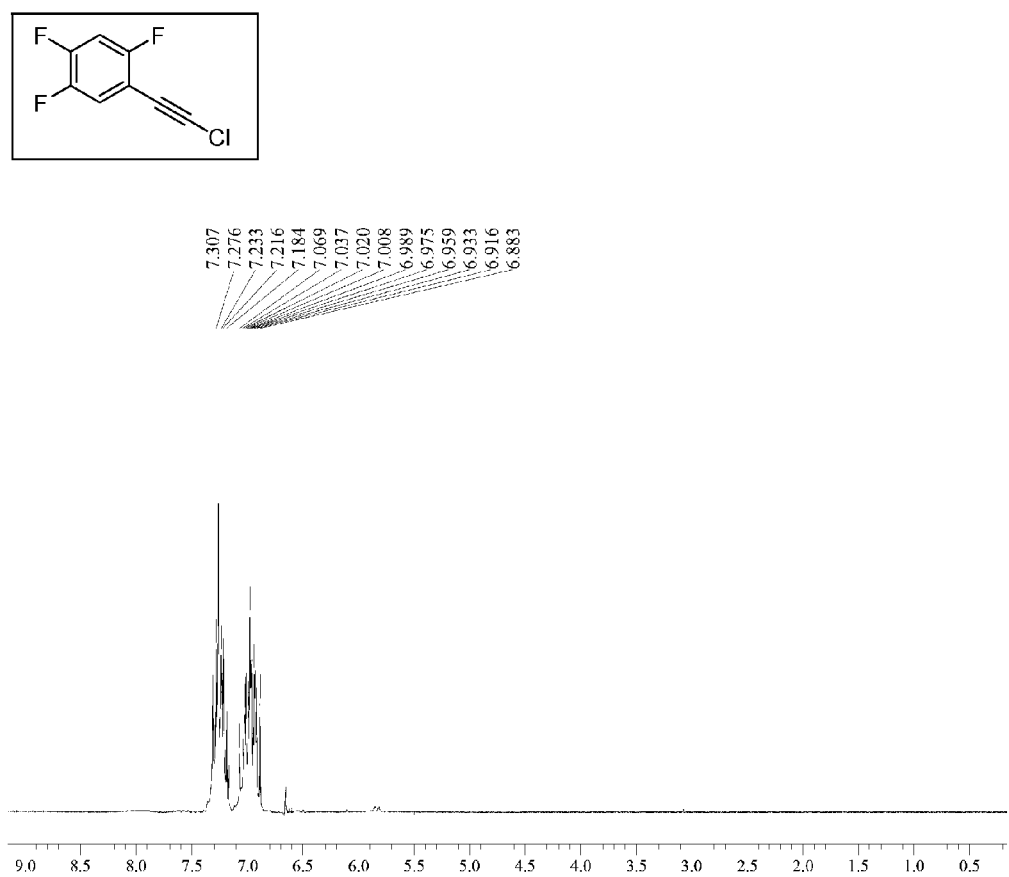

By way of example:
FIG. 1 shows a general diagram of the process according to the present invention.
FIG. 2 shows the 1H-NMR spectrum of the compound of formula (IV) in which X is Cl.

DETAILED DESCRIPTION OF THE INVENTION

The present invention relates to a process for the preparation of 2,4,5-trifluorophenylacetic acid of formula (I) or a salt thereof:

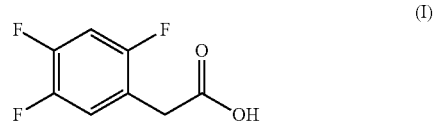 [SMILES: O=C(O)Cc1cc(F)c(F)cc1F]

comprising the following steps:
(a) halogenation of the compound of formula (VII):

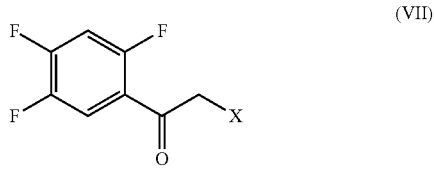

in which X is a halogen atom, to give the compound of formula (V):

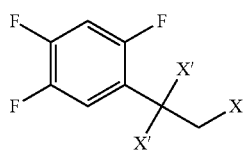

in which X and X' are independently halogen atoms, and/or the compound of formula (VI):

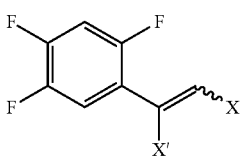

in which X and X' are independently halogen atoms,
(b) dehydrohalogenation of the compound/s obtained in the previous step to give the compound of formula (IV):

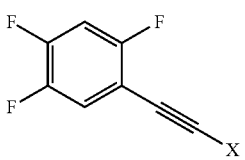

in which X is a halogen atom;
(c) conversion of the compound obtained in the previous step into the compound of formula (II):

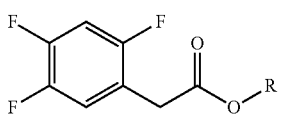

in which R is a linear or branched C1-C5 alkyl or is an aryl or benzyl group;
and/or into the compound of formula (III):

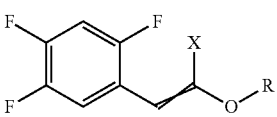

in which X is a halogen atom and R is a linear or branched C1-C5 alkyl or is an aryl or benzyl group;
(d) hydrolysis of the compound/s obtained in the previous step to give the compound of formula (I) or salts thereof:
or, alternatively to the steps (c) and (d) the following step:
(e) direct hydrolysis of the compound of formula (IV) obtained in the step (b) to give the compound of formula (I) or salts thereof.

For compound of formula (III):

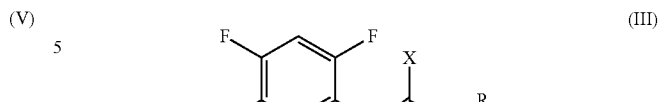

both that having the C is (Z) configuration and that having the Trans (E) configuration are meant.

According to a preferred embodiment the steps (b) and (c) may be carried out consecutively therefore without the isolation of the compound of formula (IV).

According to a further preferred embodiment the steps (c) and (d) may be carried out consecutively without the isolation of the compound of formula (II) and/or of the compound of formula (III). In addition, steps (b), (c) and (d) may be carried out consecutively without the need to isolate the intermediates of formula (IV), (III) and (II). The process according to the present invention may also comprise the further step of acylation of 1,2,4-trifluorobenzene of formula (VIII) to give the compound of formula (VII):

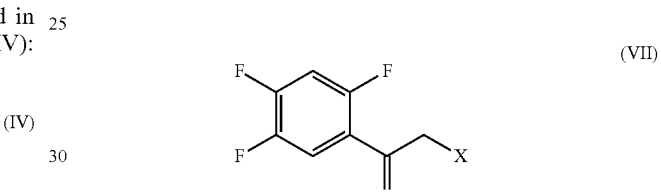

in which X is a halogen atom.

By atom of halogen in all the intermediate compounds of the present invention an atom chosen from fluorine, chlorine, bromine or iodine is meant.

In all the intermediate compounds the two atoms of halogen X and X' are independent, that is to say, may be the same or different.

According to a preferred embodiment the process of the present invention is conveniently carried out using intermediate compounds of formula (III), (IV), (V), (VI) and (VII) in which X is a chlorine atom.

According to a preferred embodiment the process of the present invention may be carried out using compounds of formula (V) and (VI) in which X' is a chlorine atom.

According to a more preferred embodiment the process of the present invention may be carried out using compounds of formula (V) and (VI) in which both X and X' are a chlorine atom.

The process of the present invention may utilise compounds of formula (III) and (II) in which R is a linear or branched C1-C5 alkyl, therefore chosen from the group comprising methyl, ethyl, n-propyl, isopropyl, n-butyl, sec-butyl, iso-butyl, tert-butyl, n-pentyl, sec-pentyl, 2-ethylpropyl, iso-pentyl, 2,2-dimethylpropyl. Preferably the process of the present invention is performed with R equal to methyl or ethyl.

The process of the present invention may also utilise compounds of formula (III) and (II) in which R is an aryl or benzyl, thus comprising for example phenyl or naphthyl.

The step (a) of the present invention is a halogenation reaction including for example a fluorination or an iodination, chlorinations and brominations being preferred. Such latter may be conveniently conducted with $PCl_5$, $POCl_3$, $PBr_3$. The halogenations are preferably carried out in organic solvent such as THF, Dioxane, DMF, NMP, DMSO, benzene, toluene, chlorobenzene, nitrobenzene, fluoro-benzenes, xylenes, fluoro-benzene being preferred.

The step (b) of dehydrohalogenation and/or the step (c) of alkoxylation of the process of the present invention may be conducted with hydroxides or alkoxides of various alkaline or alkaline-earth metals, such as for example NaOH or KOH. In particular KOH or a linear or branched C1-C5 alkaline or earth-alkaline alkoxide may preferably be used.

Said steps of synthesis are conducted in the presence of an organic solvent such as THF, Dioxane, DMF, NMP, DMSO, dimethoxyethane and alcohols, preferably such solvent is a linear or branched C1-C5 alcohol. Preferably it is possible to use Methanol and Ethanol.

According to a variation of the process according to the present invention, the intermediate of formula (IV) may be converted directly, according to step (e), to a product of formula (I). To such purpose an acid hydrolysis of the compound of formula (IV) is preferably used, which is preferably carried out by means of concentrated sulphuric acid.

The following compounds are new intermediates of the process of synthesis according to the present invention: intermediate of formula (II)

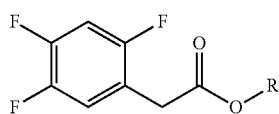

(II)

in which R is a linear or branched C3-C5 alkyl or is an aryl or benzyl group;
intermediate of formula (III)

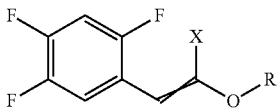

(III)

in which X is a halogen atom and R is a linear or branched C1-C5 alkyl or is an aryl or benzyl group;
intermediate of formula (IV):

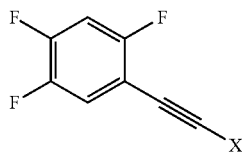

(IV)

in which X is a halogen atom;
intermediate of formula (V):

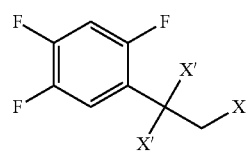

(V)

in which X and X' are independently halogen atoms, intermediate of formula (VI):

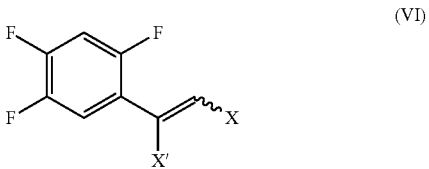

(VI)

in which X and X' are independently halogen atoms, intermediate of formula (VII):

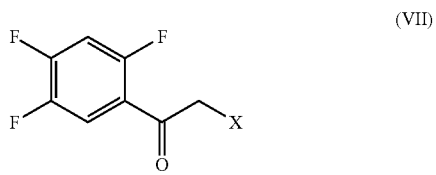

(VII)

in which X is Fluorine or Iodine.

The compounds of formula (III), (IV), (V), (VI) and (VII) in which X is a chlorine atom are preferred.

The compounds of formula (V) and (VI) in which X' is a chlorine atom are also preferred.

The compounds of formula (V) and (VI) in which both X and X' are chlorine atoms are even more preferred.

The intermediate compounds as described above are thus conveniently used for the preparation of the compound of formula (I) or salts thereof.

The 2,4,5-trifluorophenylacetic acid of formula (I) or the salts thereof prepared according to the process of the present invention may be conveniently used for the preparation of Sitagliptin according to the methods of the prior art.

EXPERIMENTAL PART

Example 1

Synthesis of 2-Chloro-1-(2,4,5-trifluorophenyl)ethanone of Formula VII—X=Cl—illustrative of the invention according to preferred aspects.
Synthesis Diagram

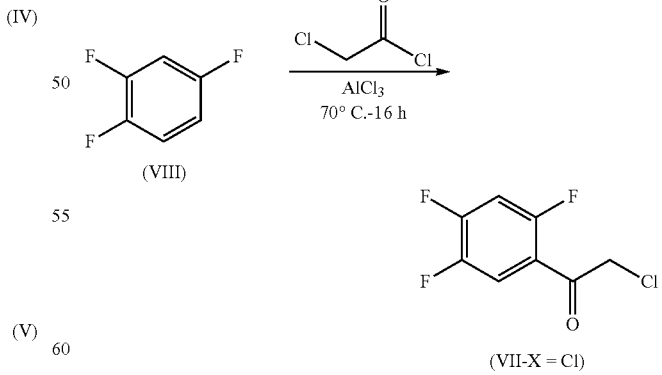

A mixture of 1,2,4-trifluorobenzene (15 ml, 144 mmol) of formula (VIII), chloroacetyl chloride (11.5 ml, 145 mmol) and aluminium trichloride (38.3 g, 285 mmol) was stirred at 70° C. for 16 h. It was then neutralised with aqueous saturated $Na_2CO_3$. The resulting mixture was extracted with $Et_2O$ (3×30 ml) and the combined organic phases were washed with an aqueous solution of NaHCO₃ (30 ml) and brine (30 ml), then dried with MgSO₄ and concentrated in the rotary evaporator. The residue was further purified by sublimation obtaining 27.1 g of colourless crystalline product with a molar yield of 93%.

Example 2

Synthesis of 1,2,4-trifluoro-5-(1,1,2-trichloroethyl)benzene of Formula V—X=Cl, X'=Cl and 1-[(E/Z)-1,2-dichloroethenyl]-2,4,5-trifluorobenzene of formula VI—X=Cl, X'=Cl—Step (a) of the invention: Halogenation by Chlorination Illustrative of the Invention according to preferred aspects.

Synthesis Diagram

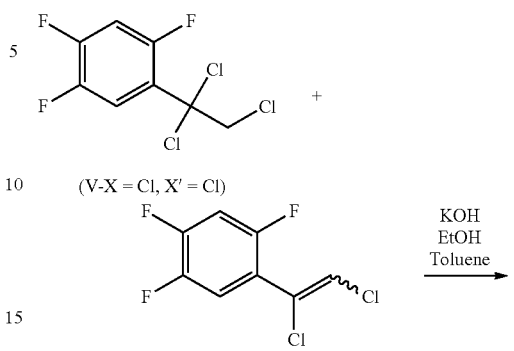

A mixture of 2-Chloro-1-(2,4,5-trifluorophenyl)ethanone of formula (VII—X=Cl) (5 g, 24 mmol) and PCl₅ (15 g, 72 mmol) in fluorobenzene (20 ml) was stirred at 80° C. for 16 h. The resulting mixture was neutralised with an aqueous saturated solution of Na₂CO and extracted with pentane (3×30 ml). The combined organic phases were washed with an aqueous solution of NaHCO₃ (30 ml) and brine (30 ml), then dried with MgSO₄ and concentrated in the rotary evaporator. 5.7 g of a colourless oil containing 1,2,4-trifluoro-5-(1,1,2-trichloroethyl)benzene of formula V—X=Cl, X'=Cl (40%, estimated via GC) and a mixture of geometric isomers E/Z of 1-[1,2-dichloroethenyl]-2,4,5-trifluorobenzene of formula VI—X=Cl, X'=Cl (60%, estimated via GC) were obtained. The conversion of the starting compound of formula VII—X=Cl into the aforesaid three compounds proved to be quantitative.

Example 3

Synthesis of (E/Z)-1-Chloro-2-(2,4,5-trifluorophenyl)ethenyl ethyl ether of formula III—X=Cl, R=Et and ethyl ester of the 2,4,5-trifluorophenylacetic acid of formula II—R=Et—one-pot step (b)+(c) of the invention: dehydrohalogenation+alkoxylation illustrative of the invention according to preferred aspects.

Synthesis Diagram

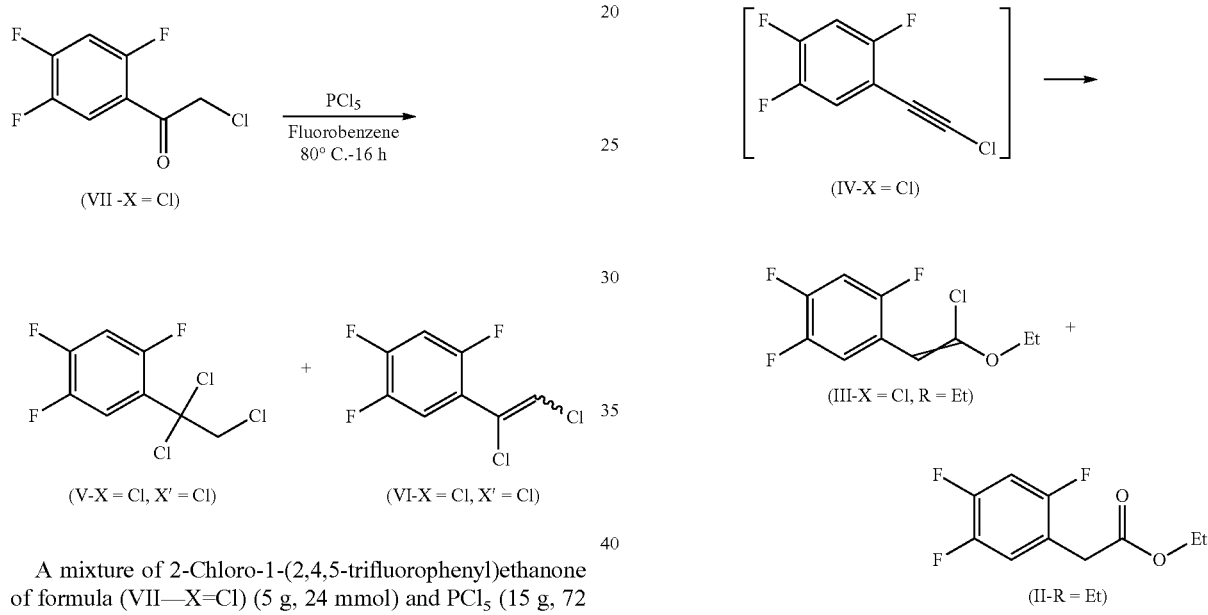

The mixture of chlorination products of example 2 (118 mg, 0.4 mmol) and EtOH (0.23 ml, 4 mmol) was added to a suspension of KOH (112 mg, 2 mmol) in toluene (2 ml). The resulting mixture was stirred under Argon at 80° C. for 4 hours. HCl 1M (2 ml) and Et₂O (2 ml) were added at the end. The organic phase was concentrated to dryness. GC analysis of the mixture with the internal standard (Tetradecane) shows the 41% molar formation of ethyl ester of the 2,4,5-trifluorophenylacetic acid of formula II—R=Et and 20% molar of mixture of geometric isomers E/Z of 1-Chloro-2-(2,4,5-trifluorophenyl)ethenyl ethyl ether of formula III—X=Cl, R=Et.

The 1H-NMR (300 MHz, CDCl₃) spectrum of the compound of formula IV—X=Cl is shown: δ=7.18-7.31 (m, 1H), 6.88-7.07 (m, 1H) (see FIG. 2).

Example 4

Synthesis of the 2,4,5-trifluorophenylacetic acid (I)—one-pot step (b)+(c)+(d) according to the invention: dehydrohalogenation+alkoxylation+hydrolysis, illustrative of the invention according to preferred aspects.

Synthesis Diagram

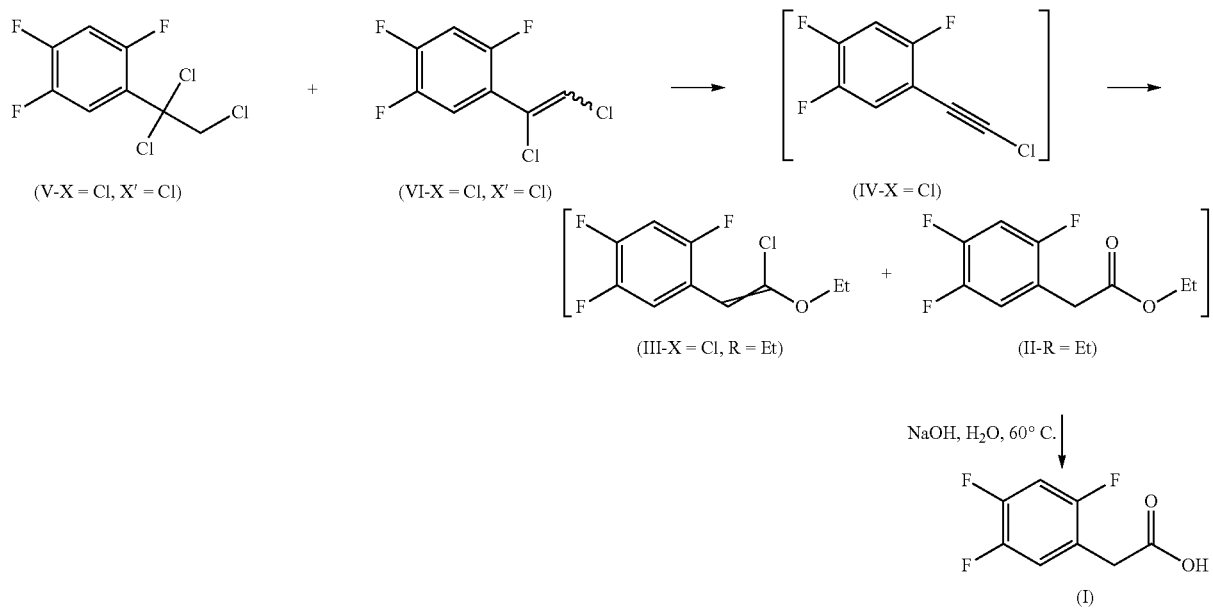

The mixture of chlorination products of example 2 (118 mg, 0.4 mmol) and EtOH (0.23 ml, 4 mmol) was added to a suspension of KOH (112 mg, 2 mmol) in toluene (2 ml) and the resulting mixture was stirred under Argon at 80° C. for 4 hours. The solvent was removed under a vacuum and a solution of NaOH 2 M (2 ml) was added at the end. The mixture was agitated at 60° C. observing the complete hydrolysis of ethyl ester of the 2,4,5-trifluorophenylacetic acid of formula II—R=Et and the formation of the 2,4,5-trifluorophenylacetic acid of formula (I).

Example 5

Synthesis of the 2,4,5-trifluorophenylacetic acid of formula (I)—Step/variation (e) of the invention: acid hydrolysis, illustrative of the invention.
Synthesis Diagram

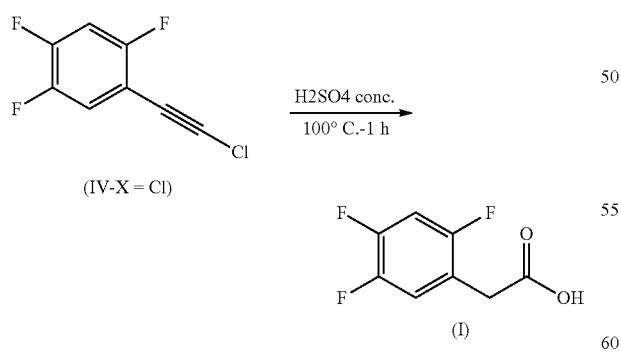

50 ml of concentrated sulphuric acid was added to 1-chloroethynyl-2,4,5-trifluorobenzene of formula IV, X=Cl and the mixture heated to 100° C. and left to stir for 1 hour. 50 ml of MTBE and 100 ml of water were then added. The phases were separated and the aqueous phase was re-extracted with 2×50 ml of MTBE. The combined organic phases were counter extracted with 3×50 ml of aqueous NaHCO$_3$ and put to one side. The three aqueous phases of NaHCO$_3$ were recombined and the resulting phase was acidified with hydrochloric acid and then extracted with 3×50 ml of MTBE. The organic phases were concentrated to a residue obtaining 0.25 g of 2,4,5-trifluorophenylacetic acid of formula (I) with a molar yield of 25%.

On the basis of the description above, a person skilled in the art may appreciate the advantages offered by the process according to the present invention; in particular the process of the present invention may lead to a 2,4,5-trifluorophenylacetic acid product in just two steps of synthesis which, among other things, entail very low cost industrial reactions. Both the operativity and the cost of the raw materials of the process according to the invention is extremely limited making such process of great interest for its application on an industrial scale.

The invention claimed is:
1. The following compounds:
intermediate of formula (II)

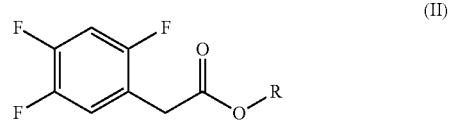

in which R is a linear or branched C3-C5 alkyl or is an aryl or benzyl group;
intermediate of formula (III)

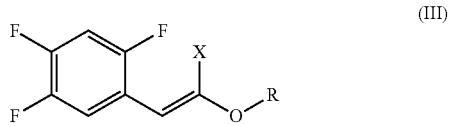

in which X is a halogen atom and R is a linear or branched C1-C5 alkyl or is an aryl or benzyl group;

intermediate of formula (IV):

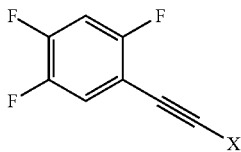
(IV)

in which X is a halogen atom;

intermediate of formula (V):

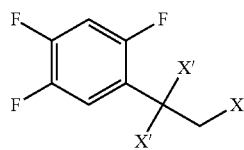
(V)

in which X and X' are independently halogen atoms, intermediate of formula (VI):

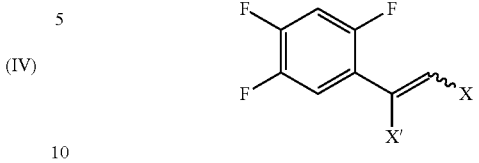
(VI)

in which X and X' are halogen atoms, where X and X' are not the same halogen atom when either X or X' is Cl, intermediate of formula (VII):

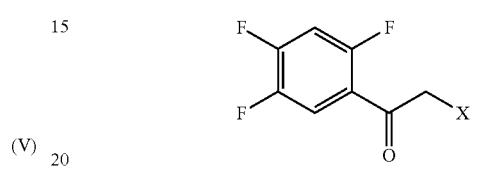
(VII)

in which X is Fluorine.

2. Compound according to the claim 1 in which in the compounds of formula (III), (IV), (V), and (VI) X is a chlorine atom.

3. Compound according to claim 1 in which in the compounds of formula (V) and (VI) X' is a chlorine atom.

* * * * *